United States Patent
Chiba et al.

(10) Patent No.: US 10,696,878 B2
(45) Date of Patent: Jun. 30, 2020

(54) FLUORENE DERIVATIVE, METHOD FOR PRODUCING THE SAME, RESIN COMPOSITION, AND ARTICLE

(71) Applicants: DEXERIALS CORPORATION, Shinagawa-ku, Tokyo (JP); KINKI UNIVERSITY, Higashiosaka-shi, Osaka (JP)

(72) Inventors: Hiroto Chiba, Tokyo (JP); Tetsuya Abe, Tokyo (JP); Sungkil Lee, Tokyo (JP); Makiya Ito, Tokyo (JP); Takeshi Endo, Iizuka (JP)

(73) Assignees: DEXERIALS CORPORATION, Tokyo (JP); KINKI UNIVERSITY, Osaka (JP)

( * ) Notice: Subject to any disclaimer, the term of this patent is extended or adjusted under 35 U.S.C. 154(b) by 170 days.

(21) Appl. No.: 15/878,845

(22) Filed: Jan. 24, 2018

(65) Prior Publication Data
US 2018/0215969 A1    Aug. 2, 2018

(30) Foreign Application Priority Data

Jan. 27, 2017   (JP) .................................. 2017-013539

(51) Int. Cl.
| | | |
|---|---|---|
| *C09J 163/00* | (2006.01) |
| *C07D 407/12* | (2006.01) |
| *C08G 59/24* | (2006.01) |
| *C08G 59/40* | (2006.01) |
| *C08G 59/68* | (2006.01) |

(52) U.S. Cl.
CPC .......... *C09J 163/00* (2013.01); *C07D 407/12* (2013.01); *C08G 59/24* (2013.01); *C08G 59/40* (2013.01); *C08G 59/68* (2013.01)

(58) Field of Classification Search
None
See application file for complete search history.

(56) References Cited

U.S. PATENT DOCUMENTS

| | | | | |
|---|---|---|---|---|
| 5,633,331 A * | 5/1997 | Nichols | ................... | C08L 69/00 525/462 |
| 2004/0245511 A1* | 12/2004 | Fujimori | ................. | C08L 69/00 252/582 |
| 2008/0085955 A1* | 4/2008 | Yanagida | ................ | C08L 67/02 524/90 |
| 2010/0048855 A1* | 2/2010 | Kato | ................... | C08G 64/1608 528/201 |

FOREIGN PATENT DOCUMENTS

JP        10-182812        7/1998
JP        2014196289 A  *  10/2014

* cited by examiner

*Primary Examiner* — Ana L. Woodward
(74) *Attorney, Agent, or Firm* — Carmody Torrance Sandak & Hennessey LLP

(57) ABSTRACT

A fluorene derivative represented by General Formula (1) below.

$$X^1-Y-X^2 \qquad \text{General Formula (1)}$$

In the General Formula (1), $X^1$ represents a cyclic carbonate group including a carbonate bond [—O—C(=O)—O—], $X^2$ represents a cyclic carbonate group including a carbonate bond [—O—C(=O)—O—], and Y represents a bivalent group including a 9,9-bisaryl fluorene skeleton.

11 Claims, 2 Drawing Sheets

FLUORENE DERIVATIVE, METHOD FOR PRODUCING THE SAME, RESIN COMPOSITION, AND ARTICLE

BACKGROUND OF THE INVENTION

Field of the Invention

The present invention relates to a fluorene derivative, a method for producing the same, a resin composition, and an article.

Description of the Related Art

Conventionally, as an adhesive material, vinyl monomers (e.g., acrylic materials) and thermosetting resins (e.g., epoxy resins and phenol resins) have been used.

However, these vinyl monomers and thermosetting resins generate volume shrinkage during polymerization. Therefore, an internal stress remaining in the cured product generates cracks to lower adhesive strength, which is problematic.

In order to solve this problem, use of a cyclic monomer as the adhesive material has been considered. It is known that the cyclic monomer exhibits lower polymerization shrinkage compared to a vinyl monomer having the same molecular weight as that of the cyclic monomer. As such a cyclic monomer, for example, 5-membered ring or 6-membered ring carbonate, vinylcyclopropane, vinyloxirane, 4-methylene-1,3-dioxolane, cyclic ketene acetal, benzocyclobutene, spiro-ortho carbonate, spiro-ortho ester, vinylcyclopropane cyclic acetal, cyclic allyl sulfide, and cyclic vinyl sulfone have been known.

For example, a cyclic carbonate resin composition including components such as a norbornane cyclic carbonate compound represented by a particular chemical formula, an epoxy resin, and an amine-based anionic ring-opening polymerization initiator has been disclosed (see, for example, Japanese Patent Application Laid-Open (JP-A) No. 10-182812).

On the other hand, the adhesive material may be required to have heat resistance. For example, the adhesive material to be used for applications to electronic components such as semiconductors and multilayer printed circuit boards is required to have heat resistance.

SUMMARY OF THE INVENTION

The present invention solves the aforementioned problem in the art and aims to achieve the following object. Specifically, an object of the present invention is to provide a fluorene derivative achieving heat resistance and low cure shrinkage, a method for producing the same, a resin composition including the fluorene derivative, and an article using the fluorene derivative.

Means for solving the problems are as follows. That is,

<1> A fluorene derivative represented by General Formula (1) below:

$$X^1—Y—X^2 \quad \text{General Formula (1)}$$

where in the General Formula (1), $X^1$ represents a cyclic carbonate group including a carbonate bond [—O—C(=O)—O—], $X^2$ represents a cyclic carbonate group including a carbonate bond [—O—C(=O)—O—], and Y represents a bivalent group including a 9,9-bisaryl fluorene skeleton.

<2> The fluorene derivative according to <1>, wherein the bivalent group represented by the Y is a bivalent group represented by General Formula (Y1) below:

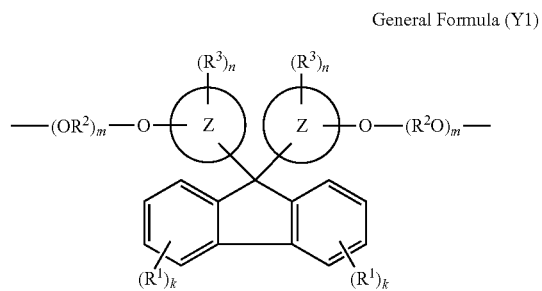

General Formula (Y1)

where in the General Formula (Y1), ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a substituted amino group, k each independently represents an integer of 0 to 4, m each independently represents an integer of 0 or 1 or to more, and n each independently represents an integer of 0 or 1 or more.

<3> The fluorene derivative according to <1> or <2>, wherein the group represented by the $X^1$ is a group represented by General Formula (X1) below and the group represented by the $X^2$ is a group represented by General Formula (X2) below:

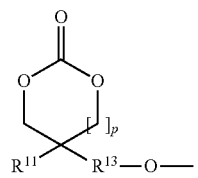

General Formula (X1)

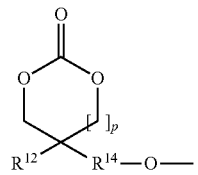

General Formula (X2)

where in the General Formula (X1), $R^{11}$ represents an alkyl group, $R^{13}$ represents an alkylene group, and p represents 0 or 1; and in the General Formula (X2), $R^{12}$ represents an alkyl group, $R^{14}$ represents an alkylene group, and p represents an integer of 0 or 1.

<4> The fluorene derivative according to any one of <1> to <3>, wherein the fluorene derivative is represented by General Formula (Z31) below:

General Formula (Z31)

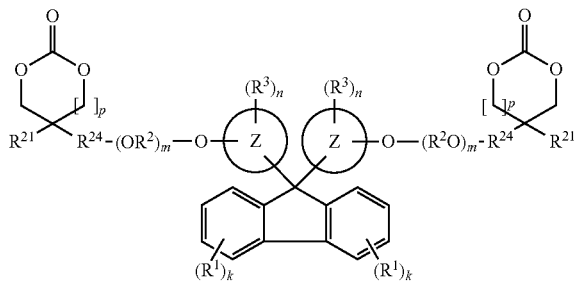

where in the General Formula (Z31), $R^{21}$ each represents an alkyl group, $R^{24}$ each represents an alkylene group, ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a substituted amino group, k each independently represents an integer of 0 to 4, m each independently represents an integer of 0 or 1 or more, n each independently represents an integer of 0 or 1 or more, and p each represents an integer of 0 or 1.

<5> The fluorene derivative according to any one of <1> to <4>, wherein the fluorene derivative is represented by General Formula (Z32) below:

General Formula (Z32)

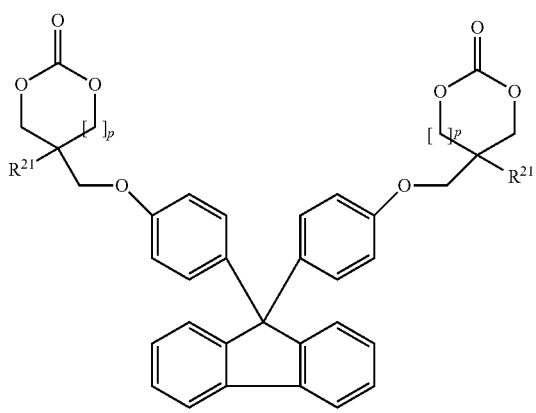

where in the General Formula (Z32), $R^{21}$ each represents an alkyl group, and p each represents an integer of 0 or 1.

<6> A method for producing a fluorene derivative, the method including: reacting a compound represented by General Formula (X3) below with a compound represented by General Formula (Y2) below to obtain a fluorene derivative represented by General Formula (21) below; converting the fluorene derivative represented by General Formula (21) into a fluorene derivative represented by General Formula (Z2) below; and converting the fluorene derivative represented by General Formula (22) into a fluorene derivative represented by General Formula (Z3) below to obtain the fluorene derivative represented by General Formula (Z3), General Formula (X3)

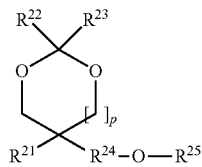

General Formula (Y2)

HO—Y—OH

General Formula (Z1)

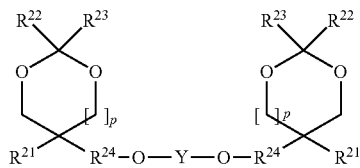

General Formula (Z2)

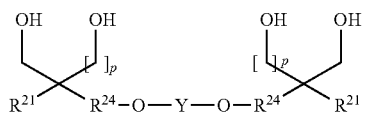

General Formula (Z3)

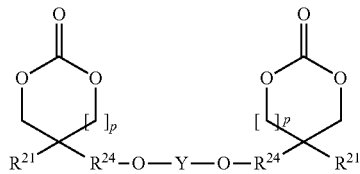

where in the General Formula (X3), the General Formula (Y2), the General Formula (Z1), the General Formula (Z2), and the General Formula (Z3), $R^{21}$ each represents an alkyl group, $R^{22}$ each represents an alkyl group, $R^{23}$ each represents an alkyl group, $R^{24}$ each represents an alkylene group, $R^{25}$ represents a substituted sulfonyl group, and Y represents a bivalent group including a 9,9-bisaryl fluorene skeleton, and p each represents an integer of 0 or 1.

<7> The method for producing the fluorene derivative according to <6>, wherein the compound represented by General Formula (Y2) is a compound represented by General Formula (Y21) below, the fluorene derivative represented by General Formula (21) is a fluorene derivative represented by General Formula (Z11) below, the fluorene derivative represented by General Formula (Z2) is a fluorene derivative represented by General Formula (Z21) below, and the fluorene derivative represented by General Formula (Z3) is a fluorene derivative represented by General Formula (Z31) below, General Formula (Y21)

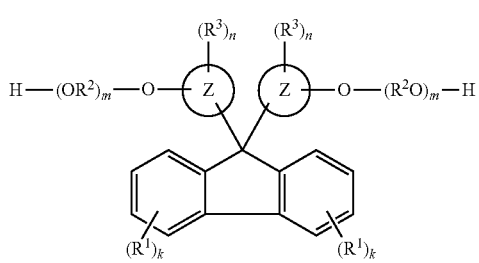

-continued

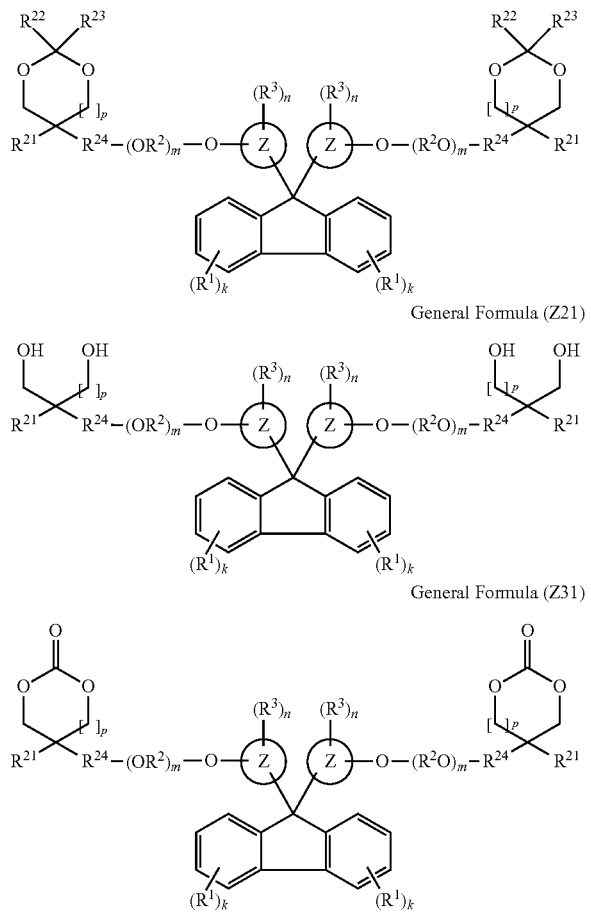

where in the General Formula (Y21), the General Formula (Z11), the General Formula (Z21), and the General Formula (Z31), $R^{21}$ each represents an alkyl group, $R^{22}$ each represents an alkyl group, $R^{23}$ each represents an alkyl group, $R^{24}$ each represents an alkylene group, ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a substituted amino group, k each independently represents an integer of 0 to 4, m each independently represents an integer of 0 or 1 or more, n each independently represents an integer of 0 or 1 or more, and p each represents an integer of 0 or 1.

<8> A resin composition including the fluorene derivative according to any one of <1> to <5>.

<9> The resin composition according to <8>, further including an epoxy compound.

<10> The resin composition according to <9>, wherein a mass ratio between the fluorene derivative and the epoxy compound (the fluorene derivative:the epoxy compound) is 0.1:99.9 to 15:85.

<11> The resin composition according to <9> or <10>, wherein the mass ratio between the fluorene derivative and the epoxy compound (the fluorene derivative:the epoxy compound) is 1:99 to 5:95.

<12> The resin composition according to any one of <8> to <11>, wherein a volume change rate before and after curing is −5.00% or less.

<13> An article including a cured product of the resin composition according to any one of <8> to <12>.

According to the present invention, it is possible to solve the problems in the art and achieve the object of the present invention. In addition, it is possible to provide a fluorene derivative achieving heat resistance and low cure shrinkage, a method for producing the same, a resin composition including the fluorene derivative, and an article using the fluorene derivative.

DESCRIPTION OF THE EMBODIMENTS (Fluorene Derivative)

Figure 1:
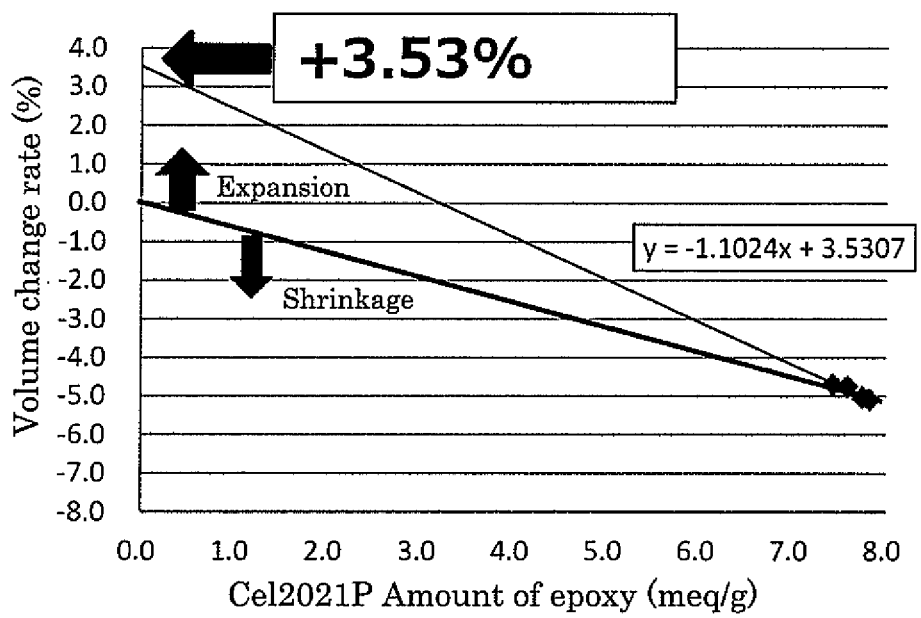
FIG. 1 is a graph for calculating a volume change rate involving no phase change of a fluorene derivative synthesized in Example 1.

A fluorene derivative of the present invention is represented by General Formula (1) below.

$$X^1-Y-X^2 \quad \text{General Formula(1)}$$

In the General Formula (1), $X^1$ represents a cyclic carbonate group including a carbonate bond [—O—C(=O)—O—], $X^2$ represents a cyclic carbonate group including a carbonate bond [—O—C(=O)—O—], and Y represents a bivalent group including a 9,9-bisaryl fluorene skeleton.

<$X^1$, $X^2$>

A group represented by the $X^1$ is not particularly limited and may be appropriately selected depending on the intended purpose, but is preferably a group represented by General Formula (X1) below.

A group represented by the $X^2$ is not particularly limited and may be appropriately selected depending on the intended purpose, but is preferably a group represented by General Formula (X2) below.

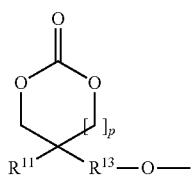

General Formula (X1)

General Formula (X2)

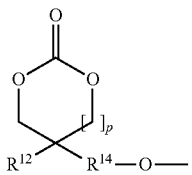

In the General Formula (X1), $R^{11}$ represents an alkyl group, $R^{13}$ represents an alkylene group, and p represents 0 or 1. In the General Formula (X2), $R^{12}$ represents an alkyl group, $R^{14}$ represents an alkylene group, and p represents an integer of 0 or 1.

The $R^{11}$ and the $R^{12}$ may be identical to or different from each other, but are preferably identical to each other.

The $R^{13}$ and the $R^{14}$ may be identical to or different from each other, but are preferably identical to each other.

An alkyl group of the $R^{11}$ and an alkyl group of the $R^{12}$ are not particularly limited and may be appropriately selected depending on the intended purpose, but are preferably an alkyl group having 1 to 6 carbon atoms, more preferably an alkyl group having 1 to 4 carbon atoms, particularly preferably an alkyl group having 1 to 2 carbon atoms.

In the present specification, a numerical range presented using "to" means such a range that the numeral described before the "to" is included in the numerical range as the minimum value and the numeral described after the "to" is included in the numerical range as the maximum value. That is, the phrase "having 1 to 6 carbon atoms" is identical to the phrase "having 1 or more but 6 or less carbon atoms".

An alkylene group of the $R^{13}$ and an alkylene group of the $R^{14}$ are not particularly limited and may be appropriately selected depending on the intended purpose, but are preferably an alkylene group having 1 to 6 carbon atoms, more preferably an alkylene group having 1 to 4 carbon atoms, still more preferably an alkylene group having 1 to 2 carbon atoms, particularly preferably a methylene group.

p in the General Formula (X1) and p in the General Formula (X2) may be identical to or different from each other, but are preferably identical to each other.

<Y>

A bivalent group represented by the Y is not particularly limited and may be appropriately selected depending on the intended purpose, but is preferably a bivalent group represented by General Formula (Y1) below.

General Formula (Y1)

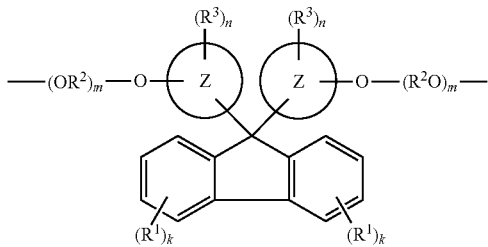

In the General Formula (Y1), ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a substituted amino group, k each independently represents an integer of from 0 to 4, m each independently represents an integer of 0 or 1 or more, and n each independently represents an integer of 0 or 1 or more.

<<Ring Z>>

Each ring Z in the General Formula (Y1) is not particularly limited and may be appropriately selected depending on the intended purpose so long as it is an aromatic hydrocarbon ring. Examples thereof include a benzene ring, a naphthalene ring, and an anthracene ring. Two rings Z may be identical to or different from each other.

<<$R^1$>>

As a substituent represented by $R^1$ in the General Formula Y1), nonreactive substituents such as a cyano group, a halogen atom (e.g., a fluorine atom, a chlorine atom, and a bromine atom), and hydrocarbon groups [e.g., an alkyl group and an aryl group ($C_{6-10}$ aryl groups such as a phenyl group)] are exemplified. In many cases, the substituent represented by $R^1$ is particularly a halogen atom, a cyano group, or an alkyl group (particularly, an alkyl group).

Examples of the alkyl group include $C_{1-6}$ alkyl groups (for example, a $C_{1-4}$ alkyl group, particularly a methyl group) such as a methyl group, an ethyl group, a propyl group, an isopropyl group, a butyl group, and a t-butyl group.

Note that, when k is a plural number (two or more), $R^1$s may be different from or identical to each other. In addition, $R^1$s substituting the respective two benzene rings constituting the fluorene (or fluorene skeleton) may be identical to or different from each other. A site of the benzene ring constituting the fluorene to which $R^1$ is linked (site of substitution) is not particularly limited. The number of substitution k is preferably 0 to 1, particularly preferably 0. Note that, in the two benzene rings constituting the fluorene, the number of substitution k may be identical to or different from each other.

<<$R^2$>>

An alkylene group represented by $R^2$ in the General Formula (Y1) is, for example, $C_{2-6}$ alkylene groups such as an ethylene group, a propylene group (or a 1,2-propanediyl group), a trimethylene group, a 1,2-butanediyl group, and a tetramethylene group, preferably a $C_{2-4}$ alkylene group, still more preferably a $C_{2-3}$ alkylene group. Particularly, among these alkylene groups, branched alkylene groups (e.g., a branched $C_{3-4}$ alkylene group) such as a propylene group surprisingly has a higher effect on reducing viscosity of the fluorene derivative represented by the General Formula (1), compared to, for example, an ethylene group.

Note that, when m is 2 or more, alkylene groups may be different alkylene groups and generally may be alkylene groups that are identical to each other. In addition, in two hydrocarbon rings, $R^2$s may be identical to or different from each other. Generally, $R^2$s may be identical to each other.

The number of the oxyalkylene groups ($OR^2$) (number of moles added) m can be selected from a range of 0 to 15 (for example, 0 to 12). For example, the number of the oxyalkylene groups ($OR^2$) (number of moles added) m may be, for example, 0 to 8, preferably 0 to 6, more preferably 0 to 4 (for example, 0 to 3), particularly preferably 0 to 2.

Note that, ms, which are the number of the substitution, in different rings Z may be identical to or different from each other.

In addition, the sum of the oxyalkylene groups (m×2) in the two rings Z can be selected from a range of 0 to 30 (for example, 0 to 24). The sum of the oxyalkylene groups (m×2) in the two rings Z may be, for example, 0 to 16 (for example, 0 to 14), preferably 0 to 12 (for example, 0 to 10), more preferably 0 to 8 (for example, 0 to 6), particularly 0 to 4 (for example, 0 to 3).

<<$R^3$>>

Examples of the hydrocarbon group include an alkyl group (e.g., $C_{1-20}$ alkyl groups such as a methyl group, an ethyl group, a propyl group, an isopropyl group, a butyl group, an s-butyl group, and a t-butyl group, preferably a $C_{1-8}$ alkyl group, more preferably a $C_{1-6}$ alkyl group), a cycloalkyl group ($C_{5-10}$ cycloalkyl groups such as a cyclopentyl group and a cyclohexyl group, preferably a $C_{5-8}$ cycloalkyl group, more preferably a $C_{5-6}$ cycloalkyl group), an aryl group [e.g., a phenyl group, an alkylphenyl group [a methylphenyl group (or, for example, a tolyl group, a 2-methylphenyl group, a 3-methylphenyl group), a dimethylphenyl group (a xylyl group)], $C_{6-10}$ aryl groups such as a naphthyl group, preferably a $C_{6-8}$ aryl group, particularly a phenyl group], an aralkyl group (e.g., $C_{6-10}$ aryl-$C_{1-4}$ alkyl groups such as a benzyl group and a phenethyl group).

Examples of the alkoxy group include $C_{1-20}$ alkoxy groups such as a methoxy group, an ethoxy group, a propoxy group, an n-butoxy group, an isobutoxy group, and a t-butoxy group. The alkoxy group is preferably a $C_{1-8}$ alkoxy group, more preferably a $C_{1-6}$ alkoxy group.

Examples of the cycloalkoxy group include $C_{5-10}$ cycloalkyloxy groups such as a cyclohexyloxy group.

Examples of the aryloxy group include $C_{6-10}$ aryloxy groups such as a phenoxy group.

Examples of the aryloxy group include $C_{6-10}$ aryl-$C_{1-4}$ alkyloxy groups such as a benzyloxy group.

Examples of the alkylthio group include $C_{1-20}$ alkylthio groups such as a methylthio group, an ethylthio group, a propylthio group, an n-butylthio group, and a t-butylthio group. The alkylthio group is preferably a $C_{1-8}$ alkylthio group, more preferably a $C_{1-6}$ alkylthio group.

Examples of the cycloalkylthio group include $C_{5-10}$ cycloalkylthio groups such as a cyclohexylthio group.

Examples of the arylthio group include $C_{6-10}$ arylthio groups such as a thiophenoxy group.

Examples of the aralkylthio group include $C_{6-10}$ aryl-$C_{1-4}$ alkylthio groups such as a benzylthio group.

Examples of the acyl group include $C_{1-6}$ acyl groups such as an acetyl group.

Examples of the alkoxycarbonyl group include $C_{1-4}$ alkoxy-carbonyl groups such as a methoxycarbonyl group.

Examples of the halogen atom include a fluorine atom, a chlorine atom, a bromine atom, and an iodine atom.

Examples of the substituted amino group include a dialkylamino group.

Among them, the substituent $R^3$ is preferably a hydrocarbon group, an alkoxy group, a cycloalkoxy group, an aryloxy group, an aralkyloxy group, an acyl group, a halogen atom, a nitro group, a cyano group, and a substituted amino group, particularly preferably a hydrocarbon group [e.g., an alkyl group (for example, $C_{1-6}$ alkyl group)], an alkoxy group (for example, a $C_{1-4}$ alkoxy group), a halogen atom (for example, a fluorine atom, a chlorine atom, a bromine atom, and an iodine atom).

In the single ring Z, when n is a plural number (two or more), substituents $R^3$ may be different from or identical to each other. Moreover, in two rings Z, the substituents $R^3$ may be identical to or different from each other. In addition, the preferable number of substitution n may be 0 to 8, preferably 0 to 6 (for example, 1 to 5), more preferably 0 to 4, particularly preferably 0 to 2 (for example, 0 to 1). In the two rings Z, the number of the substitution n may be identical to or different from each other.

The fluorene derivative is preferably a fluorene derivative represented by General Formula (Z3) below, more preferably a fluorene derivative represented by General Formula (Z31) below, particularly preferably a fluorene derivative represented by General Formula (Z32) below.

General Formula (Z3)

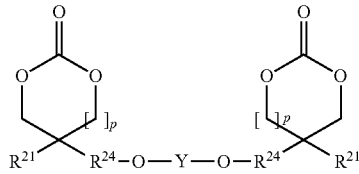

General Formula (Z31)

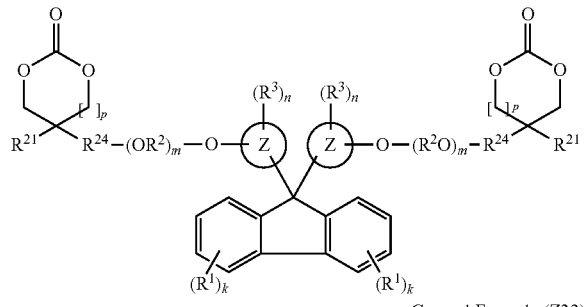

General Formula (Z32)

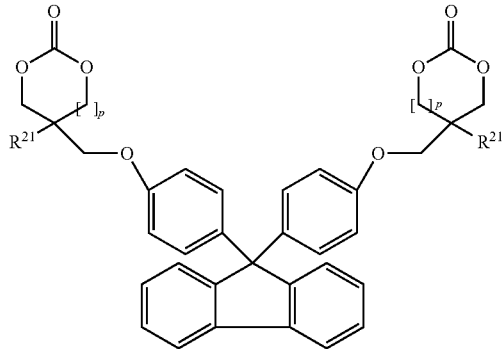

In the General Formula (Z3), the General Formula (Z31), and the General Formula (Z32), $R^{21}$ each represents an alkyl group, $R^{24}$ each represents an alkylene group, p each represents an integer of 0 or 1, and other substituents and the number of repeating units (k, m, n, p) are the same as exemplified in the description of the substituents and the number of repeating units (k, m, n, p) in the General Formula (1) and the General Formula (Y1).

An alkyl group of the $R^{21}$ is not particularly limited and may be appropriately selected depending on the intended purpose, but is preferably an alkyl group having 1 to 6 carbon atoms, more preferably an alkyl group having 1 to 4 carbon atoms, particularly preferably an alkyl group having 1 to 2 carbon atoms.

An alkylene group of the $R^{24}$ is not particularly limited and may be appropriately selected depending on the intended purpose, but is preferably an alkylene group having 1 to 6 carbon atoms, more preferably an alkylene group having 1 to 4 carbon atoms, still more preferably an alkylene group having 1 to 2 carbon atoms, particularly preferably a methylene group.

A method for producing the fluorene derivative is not particularly limited and may be appropriately selected depending on the intended purpose. However, the following method is preferable in terms of excellence in a yield rate.
(Method for Producing Fluorene Derivative)

A method of the present invention for producing a fluorene derivative includes at least a first step, a second step, and a third step, further includes other steps if necessary.
<First Step>

The first step is not particularly limited and may be appropriately selected depending on the intended purpose, so long as it is a step of reacting a compound represented by General Formula (X3) below with a compound represented by General Formula (Y2) below to obtain a fluorene derivative represented by General Formula (Z1) below.

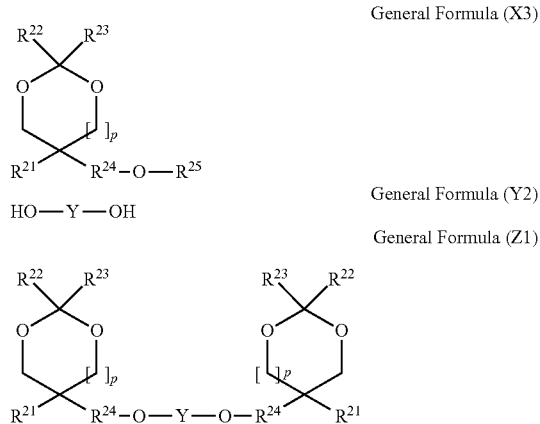

General Formula (X3)

General Formula (Y2)

General Formula (Z1)

In the General Formula (X3), the General Formula (Y2), and the General Formula (Z1), $R^{21}$ each represents an alkyl group, $R^{22}$ each represents an alkyl group, $R^{23}$ each represents an alkyl group, $R^{24}$ each represents an alkylene group, $R^{25}$ represents a substituted sulfonyl group, and Y represents a bivalent group including a 9,9-bisaryl fluorene skeleton, and p each represents an integer of 0 or 1.

<<$R^{21}$>>

An alkyl group of the $R^{21}$ is not particularly limited and may be appropriately selected depending on the intended purpose, but is preferably an alkyl group having 1 to 6 carbon atoms, more preferably an alkyl group having 1 to 4 carbon atoms, particularly preferably an alkyl group having 1 to 2 carbon atoms.

<<$R^{22}$>>

An alkyl group of the $R^{22}$ is not particularly limited and may be appropriately selected depending on the intended purpose, but is preferably an alkyl group having 1 to 6 carbon atoms, more preferably an alkyl group having 1 to 4 carbon atoms, particularly preferably an alkyl group having 1 to 2 carbon atoms.

<<$R^{23}$>>

An alkyl group of the $R^{23}$ is not particularly limited and may be appropriately selected depending on the intended purpose, but is preferably an alkyl group having 1 to 6 carbon atoms, more preferably an alkyl group having 1 to 4 carbon atoms, particularly preferably an alkyl group having 1 to 2 carbon atoms.

<<$R^{24}$>>

An alkylene group of the $R^{24}$ is not particularly limited and may be appropriately selected depending on the intended purpose, but is preferably an alkylene group having 1 to 6 carbon atoms, more preferably an alkylene group having 1 to 4 carbon atoms, still more preferably an alkylene group having 1 to 2 carbon atoms, particularly preferably a methylene group.

<<$R^{25}$>>

Examples of the substituted sulfonyl group of the $R^{25}$ include a substituted or unsubstituted arylsulfonyl group and a substituted or unsubstituted alkylsulfonyl group.

Examples of the substituted or unsubstituted arylsulfonyl group include a para-toluenesulfonyl group.

Examples of the substituted or unsubstituted alkylsulfonyl group include a methanesulfonyl group.

The first step is not particularly limited and may be appropriately selected depending on the intended purpose. One specific example of the first step is as follows. Specifically, the compound represented by General Formula (Y2) is allowed to react with alkali metal alkoxide to be converted into a compound represented by General Formula (Y2') below. Then, the compound represented by General Formula (Y2') is allowed to react with a compound represented by the General Formula (X3) to obtain a fluorene derivative represented by the General Formula (Z1). This method may be performed without purifying the compound represented by General Formula (Y2').

MO—Y—OM      General Formula (Y2')

In the General Formula (Y2'), Y represents a bivalent group including a 9,9-bisaryl fluorene skeleton and M represents an alkali metal (e.g., sodium and potassium).

Examples of the alkali metal alkoxide include sodium methoxide, sodium ethoxide, sodium t-butoxide, potassium methoxide, potassium ethoxide, and potassium t-butoxide.

The first step may be performed in the presence of an organic solvent.

The organic solvent is not particularly limited and may be appropriately selected depending on the intended purpose. Examples thereof include tetrahydrofuran and dimethylsulfoxide. These may be used alone or in combination.

A reaction temperature in the first step is not particularly limited and may be appropriately selected depending on the intended purpose. For example, a temperature at which the compound represented by General Formula (Y2) is allowed to react with alkali metal alkoxide is 20° C. to 40° C. When the compound represented by General Formula (Y2') is allowed to react with the compound represented by General Formula (X3), the first step is performed under the reflux of the organic solvent.

A reaction time in the first step is not particularly limited and may be appropriately selected depending on the intended purpose. For example, when the compound represented by General Formula (Y2) is allowed to react with alkali metal alkoxide, the reaction time is 0.1 hours to 3 hours. When the compound represented by General Formula (Y2') is allowed to react with the compound represented by General Formula (X3), the reaction time is 5 hours to 20 hours.

An amount of the compound represented by General Formula (X3) used in the first step is not particularly limited and may be appropriately selected depending on the intended purpose. However, the amount is preferably 2.0 mol to 5.0 mol, more preferably 2.1 mol to 3.0 mol, relative to an amount (1 mol) of the compound represented by General Formula (Y2).

As the compound represented by General Formula (X3), an appropriately synthesized product may be used.

As the method for obtaining the fluorine derivative represented by General Formula (X3), the following method is exemplified. Specifically, a compound represented by General Formula (X3-1) below is allowed to react with alkali metal alkoxide to be converted into a compound represented by General Formula (X3-2) below. Then, the compound represented by General Formula (X3-2) is allowed to react with a compound represented by the General Formula (B) to obtain a compound represented by General Formula (X3). This method may be performed without purification of the compound represented by General Formula (X3-2).

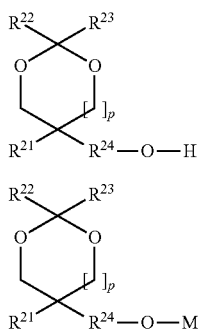

General Formula (X3-1)

General Formula (X3-2)

In the General Formula (X3-1) and the General Formula (X3-2), $R^{21}$ each represents an alkyl group, $R^{22}$ each represents an alkyl group, $R^{23}$ each represents an alkyl group, $R^{24}$ each represents an alkylene group, M represents an alkali metal (e.g., sodium and potassium), and p represents an integer of 0 or 1.

$R^{25}$—A  General Formula(B)

In the General Formula (B), $R^{25}$ represents a substituted sulfonyl group, and A represents a halogen atom (e.g., a fluorine atom, a chlorine atom, and a bromine atom).

Examples of the alkali metal alkoxide include sodium methoxide, sodium ethoxide, sodium t-butoxide, potassium methoxide, potassium ethoxide, and potassium t-butoxide.

Here, the compound represented by General Formula (X3-1) can be obtained, for example, by reacting a compound represented by the General Formula (X3-1-1) with a compound represented by General Formula (X3-1-2) below.

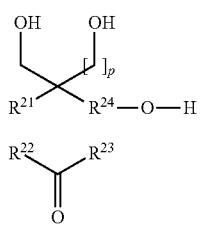

General Formula (X3-1-1)

General Formula (X3-1-2)

As the compound represented by General Formula (Y2), an appropriately synthesized product may be used and a commercially available product may be used. Examples of the commercially available product include 9,9-bis(4-hydroxyphenyl) fluorene, which is available from Tokyo Chemical Industry Co., Ltd. (TCI).

<Second Step>

The second step is not particularly limited and may be appropriately selected depending on the intended purpose so long as it is step of converting the fluorene derivative represented by General Formula (Z1) into a fluorene derivative represented by General Formula (Z2) below.

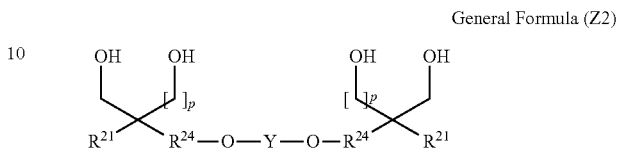

General Formula (Z2)

In the General Formula (Z2), $R^{21}$ each represents an alkyl group, $R^{24}$ each represents an alkylene group, Y represents a bivalent group including a 9,9-bisaryl fluorene skeleton, and p each represents an integer of 0 or 1.

Examples of the second step include a method for producing a hydroxyl group by releasing the compound represented by General Formula (X3-1-2) from the fluorene derivative represented by General Formula (Z1) in an acid aqueous solution.

Examples of the acid aqueous solution include a hydrochloric acid aqueous solution.

<Third Step>

The third step is not particularly limited and may be appropriately selected depending on the intended purpose so long as it is a step of converting the fluorene derivative represented by General Formula (Z2) into a fluorene derivative represented by General Formula (Z3) below to obtain the fluorene derivative represented by General Formula (Z3).

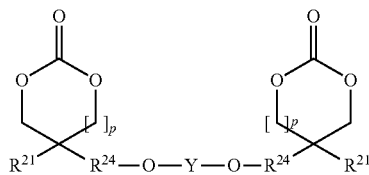

General Formula (Z3)

In the General Formula (Z3), $R^{21}$ each represents an alkyl group, $R^{24}$ each represents an alkylene group, Y represents a bivalent group including a 9,9-bisaryl fluorene skeleton, and p each represents an integer of 0 or 1.

The third step is preferably performed by reacting the fluorene derivative represented by General Formula (Z2) with a compound represented by General Formula (A) below. The compound represented by General Formula (A) is a source of carbonic acid for producing a cyclic carbonate group. As the source of carbonic acid include, other than the compound represented by General Formula (A), carbon monoxide and carbon dioxide can be used.

The third step may be performed in the presence of an organic solvent.

<<Compound Represented by General Formula (A)>>

$R^{31}$—C(=O)—$R^{32}$  General Formula (A)

In the General Formula (A), $R^{31}$ and $R^{32}$ each independently represent a halogen atom, an imidazolium group, or —O$R^{33}$ (here, $R^{33}$ is an lower alkyl group that may be substituted with a halogen atom or an aryl group that may be substituted with at least one substituent selected from the group consisting of a halogen atom, an alkoxycarbonyl group, a nitro group, a cyano group, an alkoxy group, an alkyl group, and a haloalkyl group).

Examples of the halogen atom include a fluorine atom, a chlorine atom, and a bromine atom.

Examples of the $R^{33}$ include an alkyl group having 6 or less carbon atoms or a halogen-substituted product thereof, an aryl group (e.g., benzene and naphthalene), and an aryl group substituted with one or more substituents (here, examples of the one or more substituents include a halogen atom (e.g., fluorine, chloride, and bromide), an alkoxycarbonyl group, a nitro group, a cyano group, an alkoxy group, an alkyl group, and a haloalkyl group).

Examples of the compound represented by General Formula (A) include aliphatic carbonate diester, aromatic carbonate diester, mixed carbonate diester, phosgene, triphosgene (bis(trichloromethy) carbonate), and carbonyldiimidazole (CDI).

Examples of the aliphatic carbonate diester include dimethyl carbonate, diethyl carbonate, and dibutyl carbonate.

Examples of the aromatic carbonate diester include diphenyl carbonate and dinaphthyl carbonate.

Examples of the mixed carbonate diester include methylphenyl carbonate.

Among them, dimethyl carbonate, diphenyl carbonate, and triphosgene are preferable in terms of easy availability and handling as well as safety.

An amount of the compound represented by General Formula (A) used in the third step is not particularly limited and may be appropriately selected depending on the intended purpose. The amount is preferably 2 mol or more but 20 mol or less, more preferably 5 mol or more but 15 mol or less, relative to an amount (1 mol) of the fluorene derivative represented by General Formula (Z3).

<<Organic Solvent>>

The organic solvent is not particularly limited and may be appropriately selected depending on the intended purpose. However, the organic solvent is preferably an aprotic organic solvent in order to prevent involvement in cyclization reaction to improve a yield rate.

Examples of the aprotic organic solvent include a halogen-based solvent, an ether-based solvent, an aromatic solvent, a carbonate-based solvent, acetonitrile, and ethyl acetate.

Examples of the halogen-based solvent include dichloromethane and chloroform.

Examples of the ether-based solvent include diethyl ether, tetrahydrofuran, and 1,4-dioxane.

Examples of the aromatic solvent include benzene and toluene.

Examples of the carbonate-based solvent include dimethyl carbonate, methylethyl carbonate, diethyl carbonate, dipropyl carbonate, methylpropyl carbonate, ethylpropyl carbonate, and propylene carbonate.

These organic solvents may be appropriately selected and may be used depending on reaction conditions (for example, reaction temperature, reactivity of the fluorene derivative represented by General Formula (Z2), and reactivity of the compound represented by General Formula (A)).

An amount of the organic solvent used in the third step is not particularly limited and may be appropriately selected depending on the intended purpose.

A reaction temperature in the third step is not particularly limited and may be appropriately selected depending on the intended purpose, but is preferably 50° C. to 200° C., more preferably 100° C. to 180° C., particularly preferably 120° C. to 160° C.

A reaction time in the third step is not particularly limited and may be appropriately selected depending on the intended purpose, but is preferably 0.5 hours to 100 hours, more preferably 10 hours to 70 hours, particularly preferably 20 hours to 60 hours.

The method for producing the fluorene derivative preferably includes the following aspects.

The compound represented by General Formula (Y2) is a compound represented by General Formula (Y21) below.

The fluorene derivative represented by General Formula (Z1) is a fluorene derivative represented by General Formula (Z11) below.

The fluorene derivative represented by General Formula (Z3) is a fluorene derivative represented by General Formula (Z31) below.

General Formula (Y21)

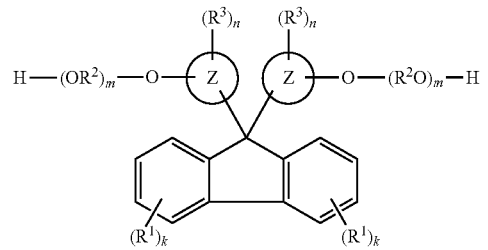

General Formula (Z11)

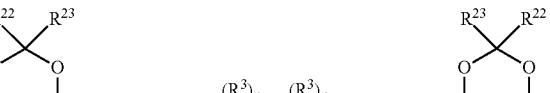

General Formula (Z21)

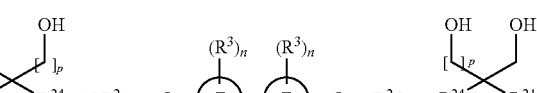

General Formula (Z31)

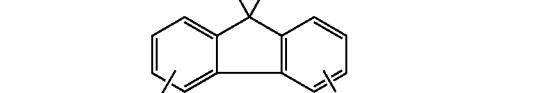

In the General Formula (Y21), the General Formula (Z11), the General Formula (Z21), and the General Formula (Z31), $R^{21}$ each represents an alkyl group, $R^{22}$ each represents an alkyl group, $R^{23}$ each represents an alkyl group, $R^{24}$ each represents an alkylene group, ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a substituted amino group, k each independently represents an integer of 0 to 4, m each independently represents an integer of 0 or 1 or more, n each independently represents an integer of 0 or 1 or more, and p each represents an integer of 0 or 1.

Details of the substituents and the number of repeating units (k, m, n, p) in the General Formula (Y21), the General Formula (Z11), the General Formula (Z21), and the General Formula (Z31) are the same as the details described in the aforementioned substituents and the number of repeating units (k, m, n, p).

(Resin Composition)

A resin composition of the present invention includes at least a fluorene derivative represented by General Formula (1) of the present invention (hereinafter may be referred to as "fluorene derivative"), preferably includes an epoxy compound, further includes other components if necessary.

<Fluorene Derivative>

An amount of the fluorene derivative in the resin composition is not particularly limited and may be appropriately selected depending on the intended purpose, but is preferably 0.1% by mass to 90% by mass, more preferably 0.5% by mass to 40% by mass, particularly preferably 1.0% by mass to 10% by mass.

<Epoxy Compound>

The epoxy compound (may be referred to as epoxy resin) is not particularly limited and may be appropriately selected depending on the intended purpose so long as it includes an epoxy group. Examples thereof include a bisphenol-type epoxy resin, polyglycidyl ether, polyglycidyl ester, an aromatic epoxy compound, an alicyclic epoxy compound, a novolac-type epoxy compound, a glycidylamine-based epoxy compound, a glycidyl ester-based epoxy compound, biphenyl diglycidyl ether, triglycidyl isocyanurate, polyglycidyl methacrylate, and a copolymer of glycidyl methacrylate and a vinyl monomer that can copolymerize with the glycidyl methacrylate.

Examples of the alicyclic epoxy compound include a cyclohexene oxide-including compound and a cyclopentene oxide-including compound.

A mass ratio (fluorene derivative:epoxy compound) of the fluorene derivative represented by General Formula (1) to the epoxy compound is not particularly limited and may be appropriately selected depending on the intended purpose. The mass ratio is preferably 0.1:99.9 to 15:85, more preferably 0.5:99.5 to 10:90, particularly preferably 1:99 to 5:95 because both heat resistance and low cure shrinkage can be achieved at a high level.

Here, the phrase "1:99 to 5:95" has the same as the meaning of "1/99 or more but 5/95 or less" as the mass ratio (fluorene derivative/epoxy compound).

An amount of the epoxy compound used in the resin composition is not particularly limited and may be appropriately selected depending on the intended purpose, but is preferably 10% by mass to 99% by mass, more preferably 30% by mass to 99% by mass, particularly preferably 50% by mass to 95% by mass.

<Other Components>

Examples of the other components include a curing agent and conductive particles.

<<Curing Agent>>

Examples of the curing agent include a cationic curing agent and an anionic curing agent.

<<<Cationic Curing Agent>>>

The cationic curing agent is not particularly limited and may be appropriately selected depending on the intended purpose, so long as it is a curing agent that generates cationic species through heat or light. Examples thereof include an onium salt.

Examples of the onium salt include a sulfonium salt and an iodonium salt.

A counter ion in the onium salt is not particularly limited and may be appropriately selected depending on the intended purpose. Examples thereof include $SbF^{6-}$, $AsF^{6-}$, $PFG^{6-}$, $BF^{4-}$, $CH_3SO^{3-}$, and $CF_3SO^{3-}$.

Examples of the iodonium salt include a diaryliodonium salt.

Examples of the diaryliodonium salt include a pentafluorophenyl borate toluyl cumyl iodonium salt.

The cationic curing agent may be a commercially available product. Examples of the commercially available product include PI2074 (available from Rhodia).

<<<Anionic Curing Agent>>>

The anionic curing agent is not particularly limited and may be appropriately selected depending on the intended purpose so long as it is a curing agent that generates anionic species through heat or light. Examples thereof include an imidazole curing agent, a polythiol curing agent, and an amine curing agent.

An amount of the cationic curing agent in the resin composition is not particularly limited and may be appropriately selected depending on the intended purpose, but is preferably 0.5 parts by mass to 10 parts by mass, more preferably 1 part by mass to 5 parts by mass, relative to the total amount of the fluorene derivative and the epoxy compound (100 parts by mass).

<<Conductive Particles>>

The conductive particles are not particularly limited and may be appropriately selected depending on the intended purpose. Examples thereof include metal particles and metal-coated resin particles.

The metal particles are not particularly limited and may be appropriately selected depending on the intended purpose. Examples thereof include nickel, cobalt, silver, copper, gold, and palladium. These may be used alone or in combination.

Among them, nickel, silver, and copper are preferable. These metal particles may be coated with gold or palladium on the surfaces thereof in order to prevent surface oxidation. Moreover, metal particles including metal projections thereon or metal particles coated with an insulating coating film (e.g., an organic compound) may be used.

The metal-coated resin particles are not particularly limited and may be appropriately selected depending on the intended purpose so long as the metal-coated resin particles are particles, such as resin particles having surfaces coated with metal. Examples thereof include particles, such as resin particles having surfaces coated with at least one metal of nickel, copper, gold, and palladium. Moreover, metal-coated resin particles including metal projections thereon or metal-coated resin particles coated with an insulating coating film (e.g., an organic compound) may be used.

A method for coating metal on the resin particles is not particularly limited and may be appropriately selected depending on the intended purpose. Examples thereof include an electroless plating method and a sputtering method.

A material of the resin particles is not particularly limited and may be appropriately selected depending on the intended purpose. Examples thereof include a styrene-divinylbenzene copolymer, a benzoguanamine resin, a cross-linked polystyrene resin, an acrylic resin, and a styrene-silica composite resin.

When the resin composition is used for anisotropic conductive connection, any conductive particles may be used so long as the conductive particles exhibit electric conductivity during the anisotropic conductive connection. For example, even when the conductive particles are particles, such as metal particles having surfaces coated with an insulating coating film, the aforementioned metal particles function as the conductive particles, so long as the particles are deformed at the time of anisotropic conductive connection to expose the metal particles.

An amount of the conductive particles in the resin composition is not particularly limited and may be appropriately selected depending on the intended purpose.

A volume change rate before and after curing of the resin composition is −5.00% or less. An upper limit of the volume change rate is not particularly limited and may be appropriately selected depending on the intended purpose. Examples of the upper limit include −1.00% and −3.00%.

The volume change rate is determined by the following formula.

$$\text{Volume change rate (\%)} = ((\text{Volume after curing}) - (\text{Volume before curing}))/(\text{Volume before curing}) \times 100(\%)$$

The volume change rate before and after curing of the resin composition can be determined by measuring a density and then regarding a reciprocal of the density as a unit volume.

In order to determine the volume change rate, a resin composition having a thickness of 125 μm is cured with UV using a metal halide lamp having a radiation dose of 1,500 mJ/cm$^2$ and is heated at 130° C. for 1 hour to obtain a cured product.

A form of the resin composition is not particularly limited and may be appropriately selected depending on the intended purpose. Examples of the form include liquid, a solid matter, and a film.

The resin composition is, for example, a curable resin composition. Examples of the curable resin composition include a thermosetting resin and a photosetting resin.

(Article)

An article of the present invention includes a cured product of the resin composition of the present invention, and further includes other members if necessary.

The article is not particularly limited and may be appropriately selected depending on the intended purpose. Examples thereof include an optical material, a molding material, a composite material, a casting material, a sealing material, a medical material, a dental material, a recording material, cement, a paint, an adhesive agent, and a material of hologram optical recording medium.

When the cured product is obtained, either heat or light may be applied to the resin composition. That is, the cured product may be obtained through either heat curing or photocuring. Moreover, the cured product may be obtained through both of heat curing and photocuring. For example, the cured product may be obtained by irradiating the resin composition with light and then heating it.

A condition for the photocuring is not particularly limited and may be appropriately selected depending on the intended purpose. Examples thereof include irradiation of ultraviolet rays having a radiation dose of 100 mJ/cm$^2$ to 10,000 mJ/cm$^2$. A source of radiation is, for example, a metal halide lamp.

A condition for the thermosetting is not particularly limited and may be appropriately selected depending on the intended purpose. Examples thereof include a heating temperature of 100° C. to 150° C. A heating time is, for example, 0.1 hours to 3 hours.

EXAMPLE

The present invention will be described in more detail by way of the following Examples. However, the present invention should not be construed as being limited to these Examples.

The product was determined for a structure and various measurements of the product were performed, under the following conditions.

<NMR Measurement>

The structure was confirmed from a $^1$H-NMR chart obtained using a nuclear magnetic resonance apparatus "JNM-ECZ400R/S3" (available from JEOL Ltd.). The measurement was performed by using any deuterated solvent and setting a cumulative number to 8.

<LC-MS Measurement>

A sample was diluted in a mixed solvent of acetonitrile/THF=9/1 (vol/vol) so as to be 0.1% by mass using UPLC (available from Waters). The measurement was performed with an amount of the injected sample being 5 μl and a flow rate being 0.4 ml/min. The MS spectrum obtained was confirmed.

<FP IR Measurement>

The IR spectrum obtained through an ATR method was confirmed using NICOLET iS10 (available from Thermo Fisher SCIENTIFIC). The measurement was performed by setting a cumulative number to 16.

<Calculation of Volume Change at the Time of Polymerization>

The sample prepared was measured for a monomer density and a polymer density using a dry-type automatic density meter (AccuPyc 11340, available from SHIMADZU CORPORATION). A reciprocal of the density was considered as a unit volume. The volume change at the time of polymerization was calculated based on the following formula.

$$((\text{Volume after curing}) - (\text{Volume before curing}))/(\text{Volume before curing}) \times 100(\%)$$

The obtained value of a positive number means the volume expansion and the obtained value of a negative number means the volume shrinkage.

<Evaluation of Glass Transition Temperature of Polymer>

A dynamic viscoelasticity measuring apparatus (name of manufacturing company: TA Instruments, product name: RSA3) was used and the cured product prepared was mounted thereon. Under the condition of an elevating rate of 10.0° C./min, the measurement was performed at a temperature range of 30° C. to 300° C. A temperature at which tan δ (loss modulus/storage modulus) obtained under the measurement condition of frequency of 10.0 Hz was the maximum point was regarded as a glass transition temperature (Tg).

<Method for Calculating Volume Change Involving No Phase Change>

The horizontal axis presents the sum of amounts of functional groups of the epoxy resin or the oxetane compound and the longitudinal axis presents a volume change rate. Values of the volume change rate were plotted on the graph. Assuming that an intercept of an approximation of root-means of the plots was regarded as 100% of TMC (trimethylene carbonate) or the synthesized product (compound expressed by Structural Formula 5), a volume change rate involving no phase change was determined.

Example 1

Synthesis Example 1: Synthesis of (5-ethyl-2,2-dimethyl-1,3-dioxan-5-yl)methanol (Compound Expressed by the Following Structural Formula 1)

In accordance with the following scheme, a compound expressed by the following Structural Formula 1 was synthesized.

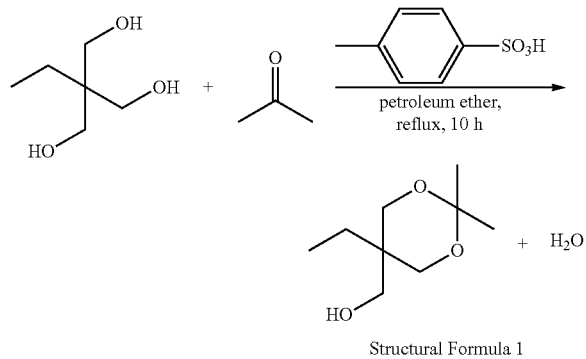

Structural Formula 1

Trimethylolpropane (53 g) (395 mmol) was dissolved in petroleum ether (120 ml) and acetone (120 ml). To the solution obtained, p-toluenesulfonic acid (monohydrate) (1.8 g) (9.4 mmol) was added and the resultant solution was heated. The solution was heated to reflux for 10 hours and then was cooled. After the resultant solution was cooled to room temperature, potassium carbonate (5 g) (36 mmol) was added thereto and was left to stand overnight. The solution obtained was filtrated and the thus-obtained filtrate was concentrated. In the residue, a compound (1) expressed by Structural Formula 1 (68.3 g) (yield rate: 99%) was obtained.

Results obtained by measuring the product through NMR are presented as below.

$^1$H-NMR (CDCl$_3$): δppm=0.82 (3H, t, J=7.6 Hz), 1.28 (2H, q, J=7.6 Hz), 1.36 (3H, s), 1.40 (3H, s), 3.61 (2H, d, J=11.6 Hz), 3.65 (2H, d, J=11.6 Hz), 3.72 (2H, s).

Synthesis Example 2: Synthesis of methyl p-toluenesulfonate (5-ethyl-2,2-dimethyl-1,3-dioxan-5-yl) (Compound Expressed by the Following Structural Formula 2)

In accordance with the following scheme, a compound expressed by the following Structural Formula 2 was synthesized.

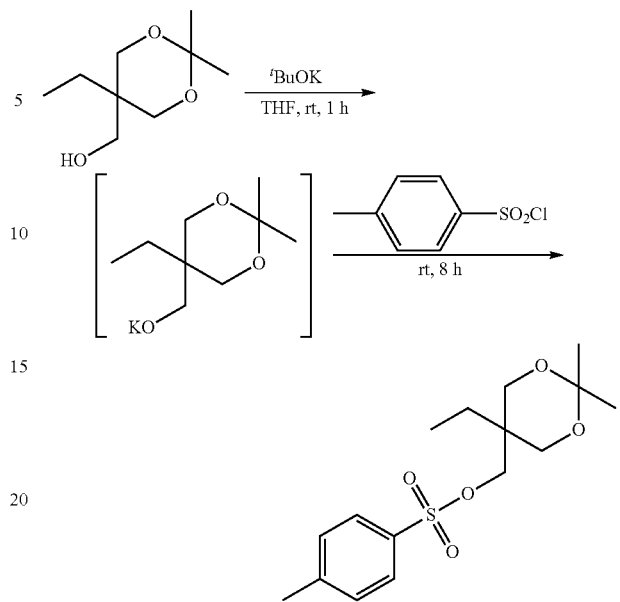

Structural Formula 2 tBuOK (14.6 g) (130 mmol) was dissolved in dehydrated THF (30 ml). Then, a solution including the compound expressed by Structural Formula 1 (20.9 g) (120 mmol) and dehydrated THF (30 ml) was slowly added dropwise thereto. After completion of the dropping, the resultant solution was stirred at room temperature for 1 hour. To the solution obtained, a solution including p-toluenesulphonyl chloride (24.0 g) (126 mmol) and dehydrated THF (40 ml) was slowly added thereto in a water bath. After completion of the dropping, the water bath was removed and the solution was stirred at room temperature for 8 hours. The solution obtained was added to a saturated sodium bicarbonate aqueous solution (200 ml) and was extracted with ethyl acetate (150 ml) two times. The ethyl acetate layer was dried with magnesium sulfate and magnesium sulfate was separated through filtration. The filtrate was concentrated. Then, ethanol (25 g) was added to the thus-obtained residue and the resultant was cooled. The precipitated crystal was filtrated and ethanol (15 g) was added to the crystal obtained. Then, the resultant was left to stand in a refrigerator (−30° C.) overnight. The precipitated crystal was filtrated and was dried in a vacuum oven at 50° C. for 3 hours to obtain a compound expressed by Structural Formula 2 (yield amount: 16.6 g, yield rate: 42%).

Results of measuring the product through NMR are presented as below.

$^1$H-NMR (CDCl$_3$): δppm=0.73 (3H, t, J=7.6 Hz), 1.20 (3H, s), 1.27 (2H, q, J=7.6 Hz), 1.34 (3H, s), 2.42 (3H, s), 3.52 (2H, d, J=11.6 Hz), 3.57 (2H, d, J=11.6 Hz), 4.11 (2H, s), 7.33 (2H, d, J=8.8 Hz), 7.79 (2H, d, J=8.8 Hz).

Synthesis Example 3: Synthesis of 9,9-bis[4-(5-ethyl-2,2-dimethyl-1,3-dioxan-5-yl)methoxyphenyl] fluorene (Compound Expressed by the Following Structural Formula 3)

In accordance with the following scheme, a compound expressed by the following Structural Formula 3 was synthesized.

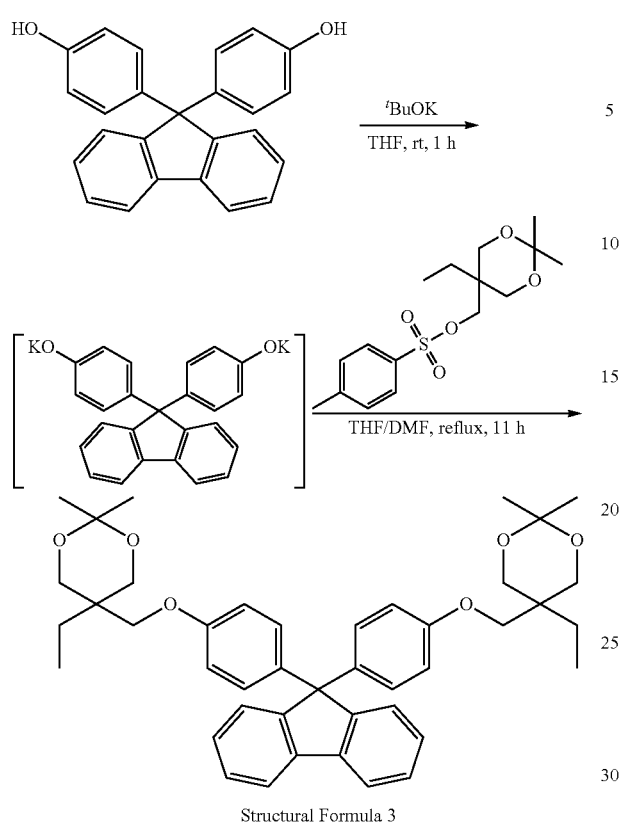

Structural Formula 3

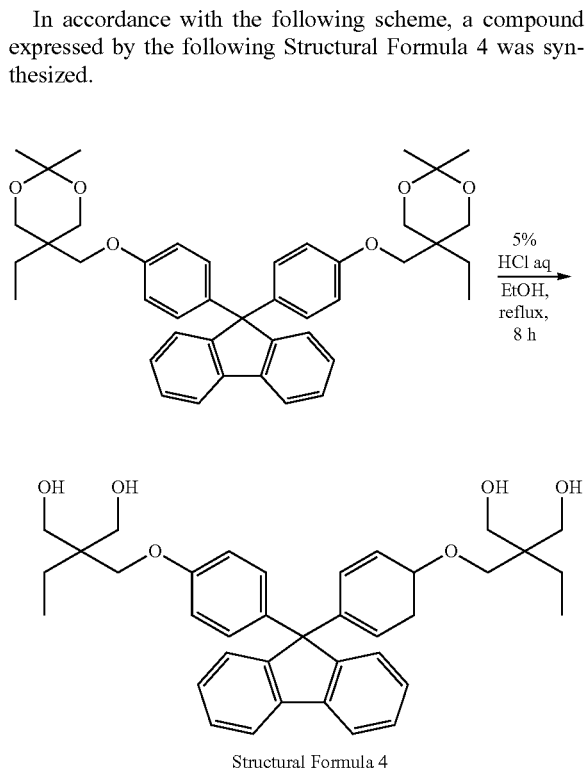

Structural Formula 4 tBuOK (5.40 g) (48 mmol) was dissolved in THF (100 ml). Then, 9,9-bis(4-hydroxyphenyl)fluorene (7.0 g) (20 mmol, available from Tokyo Chemical Industry Co., Ltd. (TCI)) was added thereto and was stirred at room temperature for 1 hour. DMF (250 ml) was added to the solution obtained and then the compound expressed by Structural Formula 2 (13.8 g) (42 mmol) was added thereto. The resultant was heated and was heated to reflux for 11 hours (at this time, THF was removed so that a temperature of the solution was 80° C. to 90° C.). After completion of the reflux, the solution was cooled to room temperature and water (400 ml) was added to the solution. The solution obtained was extracted with ethyl acetate (200 ml) two times. The ethyl acetate layer was washed with water and then with a saturated sodium bicarbonate aqueous solution. The organic layer was dried with magnesium sulfate. Magnesium sulfate was separated through filtration and the thus-obtained filtrate was concentrated. Ethanol (30 g) was added to the residue and was cooled. The precipitated crystal was filtrated and the crystal was dried in a vacuum oven at 50° C. for 6 hours to obtain a compound expressed by Structural Formula 3 (9.1 g) (yield rate: 69%).

Results of measuring the product through NMR are presented as below.

$^1$H-NMR (CDCl$_3$): δppm=0.80 (6H, t, J=8.0 Hz), 1.25 (4H, q, 8.0 Hz), 1.35 (6H, s), 1.41 (6H, s), 3.65 (4H, d, J=12.0 Hz), 3.75 (4H, d, J=12.0 Hz), 3.95 (4H, s), 6.76 (4H, d, J=8.8 Hz), 7.08 (4H, d, J=8.8 Hz), 7.24 (2H, ddd, J=1.2, 7.6, 7.6 Hz), 7.31 (2H, ddd, J=1.2, 7.6, 7.6 Hz), 7.35 (2H, dd, J=1.2, 7.6 Hz), 7.79 (2H, dd, J=1.2, 7.6 Hz).

Synthesis Example 4: Synthesis of 9,9-bis(4-(2,2-dimethylolpropyl)oxyphenyl) fluorene (Compound Expressed by the Following Structural Formula 4)

In accordance with the following scheme, a compound expressed by the following Structural Formula 4 was synthesized.

The compound expressed by Structural Formula 3 (3.5 g) (5.28 mmol) was diluted in ethanol (140 g). A 5% by mass hydrochloric acid aqueous solution (70 g) was added to the solution obtained. The solution obtained was heated and was refluxed for 8 hours. After completion of the reflux, the solution was cooled to room temperature and was left to stand overnight. The precipitated crystal was filtrated and was washed with a mixed solution of ethanol (7 ml) and water (3 ml) that had been cooled in a refrigerator. The crystal obtained was dried in a vacuum oven at 60° C. for 5 hours to obtain a compound expressed by Structural Formula 4 (3.7 g) (yield rate: 84%).

Results of measuring the product through NMR are presented as below.

$^1$H-NMR (DMSO-d6): δppm=0.79 (6H, t, J=7.6 Hz), 1.32 (4H, q, 7.6 Hz), 3.25 (8H, d, 5.1 Hz), 3.67 (4H, s), 4.36 (4H, t, J=5.1 Hz), 6.78 (4H, d, J=9.2 Hz), 6.98 (4H, d, J=9.2 Hz), 7.28 (2H, ddd, J=1.6, 8.0, 8.0 Hz), 7.34-7.38 (4H, m), 7.89 (2H, dd, J=1.6, 8.0 Hz).

Synthesis Example 5: Synthesis of (Bifunctional, Six-Membered Ring, Cyclic Carbonate Having Bisphenyl Fluorene Skeleton (Compound Expressed by the Following Structural Formula 5)

In accordance with the following scheme, a compound expressed by the following Structural Formula 5 was synthesized.

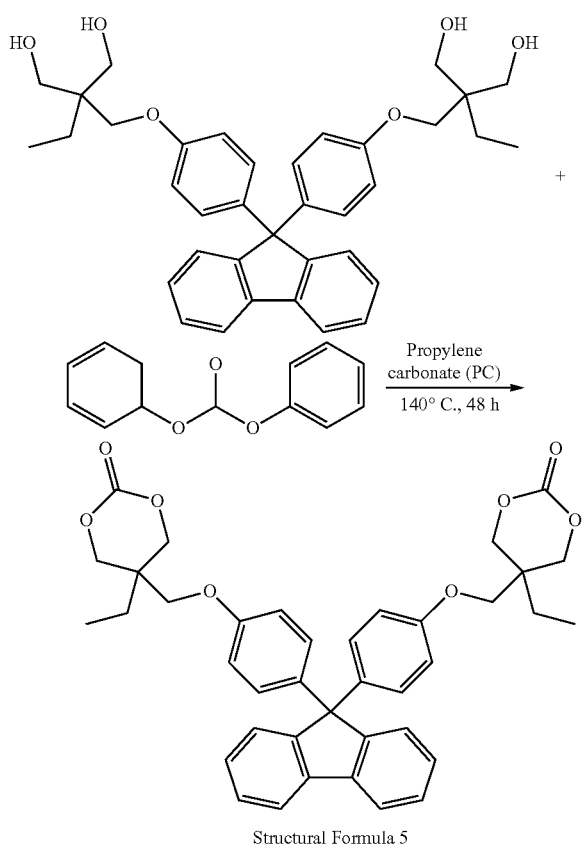

Structural Formula 5

The compound expressed by Structural Formula 4 (2.01 g) (3.45 mmol), diphenyl carbonate (DPC) (7.41 g) (34.60 mmol), and a propylene carbonate (propylene carbonate) (8.01 g) as a solvent were added to a vial bottle (50 ml). The resultant was heated for 30 minutes in an oven of 140° C. to dissolve DPC. Then, the resultant was stirred for 1 minute at room temperature and was heated for 48 hours in an oven of 140° C. Then, water (80 g) was added dropwise thereto to generate a white precipitate. The precipitate was collected through filtration and was dried in a vacuum oven of 60° C. overnight. A silica gel column with silica gel and a developing solvent of n-hexane:acetone=7:3 (volume ratio) was used to perform purification. The purification was performed with the gradient developing solvent; i.e., with the developing solvent increasing its polarity little by little. The polarity was increased in the following order: n-hexane:acetone=7:3, n-hexane:acetone=6:4, n-hexane:acetone=5:5, n-hexane:acetone, n-hexane:acetone=3:7, and n-hexane:acetone=2:8 (all of them are presented by volume ratio). After concentration of the fraction obtained, a colorless crystal was obtained. The crystal was dried in a vacuum oven of 60° C. overnight to obtain a compound expressed by Structural Formula 5 (yield amount: 2.00 g) (yield rate: 91.4%).

Results of measuring the product through NMR, LC-MS, and FT-IR are presented as below.

$^1$H-NMR (400 MHz, DMSO-d6): (ppm): 0.83 (6H, t, J=7.8 Hz), 1.48 (4H, q, J=7.6 Hz), 3.89 ppm (4H, s), 4.30 (4H, d, J=10.4 Hz), 4.34 (4H, d, J=10.4 Hz), 6.84 (4H, d, J=9.2 Hz), 7.01 (4H, d, J=8.8 Hz), 7.29 (2 Hv, ddd, J=1.2, 8.0, 8.0 Hz), 7.35-7.39 (4H, m), 7.90 (2 Hv, dd, J=0.8, 8.0 Hz)

MS(LC/MS):[2M+NH$_4$] m/z=1286.9, [M+NH$_4$] m/z=652.8

FT-IR(ATR):2972-2871 cm$^{-1}$ (CH$_2$), 1751 cm$^{-1}$ (C=O), 1173 cm-1 (C—O)

Example 2

Polymerization Example 1: Preparation of Copolymer with CEL2021P

The synthesized compound expressed by Structural Formula 5 (1 part by mass) and CEL2021P (available from Daicel Corporation, functional equivalent: 128 eq/g to 145 eq/g, 128 eq/g was employed for calculation) (99 parts by mass) were mixed and were heated at 140° C. for 1 hour to prepare a solution. The solution obtained was cooled to room temperature. Then, the solution was charged with a photocationic polymerization initiator PI2074 (available from Rhodia, pentafluorophenyl borate toluyl cumyl iodonium salt) (2 parts by mass) and was stirred until it was dissolved. The solution obtained was sandwiched with glasses that had been subjected to a release treatment with PET films of 125 μm being used as a spacer. The solution was cured with UV using a metal halide lamp having a radiation dose of 1,500 mJ/cm$^2$ and was heated at 130° C. for 1 hour to prepare a copolymer film.

A volume change rate of the film prepared was determined through density measurement and a glass transition temperature was measured based on the maximum value of tan δ in a dynamic viscoelasticity measuring apparatus.

Example 3

Polymerization Example 2: Preparation of Copolymer with CEL2021P

A copolymer film was prepared in the same manner as in Polymerization Example 1 except that the synthesized compound expressed by Structural Formula 5 (3 parts by mass) and CEL2021P (available from Daicel Corporation, functional equivalent: 128 eq/g to 145 eq/g, 128 eq/g was employed for calculation) (97 parts by mass) were mixed and were heated at 140° C. for 1 hour to prepare a solution; the solution obtained was cooled to room temperature and was charged with a photocationic polymerization initiator PI2074 (available from Rhodia) (2 parts by mass); and the resultant was stirred until it was dissolved.

A volume change rate of the film prepared was determined through density measurement and a glass transition temperature was measured based on the maximum value of tan δ in a dynamic viscoelasticity measuring apparatus.

Example 4

Polymerization Example 3: Preparation of Copolymer with CEL2021P

A copolymer film was prepared in the same manner as in Polymerization Example 1 except that the synthesized compound expressed by Structural Formula 5 (5 parts by mass) and CEL2021P (available from Daicel Corporation, functional equivalent: 128 eq/g to 145 eq/g, 128 eq/g was employed for calculation) (95 parts by mass) were mixed and were heated at 140° C. for 1 hour to prepare a solution; the solution obtained was cooled to room temperature and was charged with a photocationic polymerization initiator PI2074 (available from Rhodia) (2 parts by mass); and the resultant was stirred until it was dissolved.

A volume change rate of the film prepared was determined through density measurement and a glass transition temperature was measured based on the maximum value of tan δ in a dynamic viscoelasticity measuring apparatus.

Comparative Example 1

<Preparation of CEL2021P Copolymer>

A copolymer film was prepared in the same manner as in Polymerization Example 1 except that a photocationic polymerization initiator PI2074 (available from Rhodia) (2 parts by mass) was charged into CEL2021P (available from Daicel Corporation) (100 parts by mass) and was stirred until it was dissolved.

A volume change rate of the film prepared was determined through density measurement and a glass transition temperature was measured based on the maximum value of tan δ in a dynamic viscoelasticity measuring apparatus.

Compounding ratios of Examples 2 to 4 and Comparative Example 1 are summarized below.

TABLE 1

|  | Example 2 | Example 3 | Example 4 | Comparative Example 1 |
|---|---|---|---|---|
| CEL2021P | 99 | 97 | 95 | 100 |
| Structural Formula 5 | 1 | 3 | 5 | — |
| PI2074 | 2 | 2 | 2 | 2 |

The unit of the numerals in Table 1 is "parts by mass".

Comparative Examples 2 to 6

TMC (trimethylene carbonate, available from Tokyo Chemical Industry Co., Ltd. (TCI)), CEL2000P (available from Daicel Corporation), OXT-211 (available from Tobagosei Company, Limited), and YL-980 (available from Mitsubishi Chemical Corporation) were mixed at a ratio presented in Table 2 to prepare a solution. The solution was charged with a photocationic polymerization initiator PI2074 (available from Rhodia) (0.2 parts by mass) and was stirred until it was dissolved. The solution obtained was sandwiched with glasses that had been subjected to a release treatment with PET films of 125 μm being used as a spacer. The solution was cured with UV using a metal halide lamp having a radiation dose of 1,500 mJ/cm² and was heated at 130° C. for 1 hour to prepare a copolymer film.

A volume change rate of the film prepared was determined through density measurement and a glass transition temperature was measured based on the maximum value of tan δ in a dynamic viscoelasticity measuring apparatus.

TABLE 2

|  | Comparative Example 2 | Comparative Example 3 | Comparative Example 4 | Comparative Example 5 | Comparative Example 6 |
|---|---|---|---|---|---|
| YL-980 | 2 | 2 | 2 | 2 | 2 |
| OXT-211 (POX) | 10 | 9.64 | 9.17 | 8.81 | 7.62 |
| CEL2000 | 1 | 0.96 | 0.91 | 0.87 | 0.74 |
| TMC | — | 0.40 | 0.92 | 1.32 | 2.64 |
| PI2074 | 0.2 | 0.2 | 0.2 | 0.2 | 0.2 |

The unit of the numerals in Table 2 is "parts by mass".

Comparative Examples 7 to 10

<Preparation of Cured Product for Comparison>

A copolymer film was prepared in the same manner as in Example 4 except that the synthesized compound expressed by Structural Formula 5 was changed to a Bis-A type epoxy resin YL-980 (available from Mitsubishi Chemical Corporation) or an epoxy resin including a bisphenyl fluorene skeleton OGSOL EG-200 (available from Osaka Gas Chemicals Co., Ltd.), each of which being used at a ratio presented in Table 3; a photocationic polymerization initiator PI2074 (available from Rhodia) (2 parts by mass) was used; and the resultant was stirred at room temperature to be dissolved.

A volume change rate of the film prepared was determined through density measurement and a glass transition temperature was measured based on the maximum value of tan δ in a dynamic viscoelasticity measuring apparatus.

TABLE 3

|  | Comparative Example 7 | Comparative Example 8 | Comparative Example 9 | Comparative Example 10 |
|---|---|---|---|---|
| CEL2021P | 95 | 90 | 95 | 90 |
| YL-980 | 5 | 10 | — | — |
| OGSOL EG-200 | — | — | 5 | 10 |
| PI2074 | 2 | 2 | 2 | 2 |

The unit of the numerals in Table 3 is "parts by mass".

Volume Change Rates and Tgs of Examples 2 to 4 and Comparative Example 1

The samples prepared in Comparative Example 1 and Examples 2 to 4 were measured for the volume change rate and the glass transition temperature Tg.

Results are presented in Table 4.

<Volume Change Rate>

As a result of comparing volume change rates calculated from densities before and after curing, the volume change rate of CEL2021P of Comparative Example 1, which is used as a standard, was −5.09%. However, Examples 2 to 4, in which a part of CEL2021P was replaced with the synthesized product (compound expressed by Structural Formula 5) to copolymerize, exhibited the volume change rate of −4.98% to −4.69%, lower volume change through curing, and lower cure shrinkage than CEL2021P of the base monomer.

As a result of calculating the volume change involving no phase change, expansion of +3.5% was exhibited (FIG. 1).

<Tg>

The heat resistance was determined from a peak of tan δ of DMA. The homopolymer of CEL2021P of Comparative Example 1, which is a standard, has a Tg of 192° C. Meanwhile, Examples 2 to 4, in which a part of CEL2021P was replaced with the synthesized product (compound expressed by Structural Formula 5) to copolymerize, exhibited the Tg of 186° C. to 187° C. The copolymers of Examples 2 to 4 maintained high heat resistance that is the same degree as that of CEL2021P. It was confirmed that the present synthesized product (compound expressed by Structural Formula 5) is a novel compound that has a lower cure shrinkage and exhibits high heat resistance.

TABLE 4

|  | Example 2 | Example 3 | Example 4 | Comparative Example 1 |
|---|---|---|---|---|
| CEL2021P | 99 | 97 | 95 | 100 |
| Structural Formula 5 | 1 | 3 | 5 | — |

TABLE 4-continued

|  | Example 2 | Example 3 | Example 4 | Comparative Example 1 |
|---|---|---|---|---|
| PI2074 | 2 | 2 | 2 | 2 |
| Volume change rate (%) | −5.03 | −4.74 | −4.69 | −5.09 |
| Tg (° C.) | 186 | 187 | 187 | 192 |

The unit of the numerals in Table 4 is "parts by mass".

Volume Change Rates and Tgs of Comparative Examples 2 to 6

Figure 2:
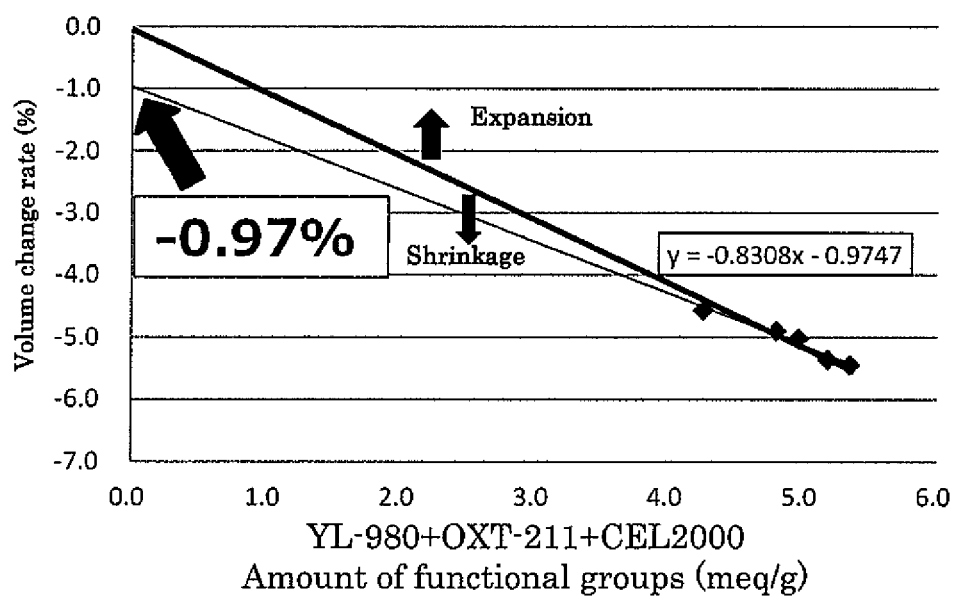
FIG. 2 is a graph for calculating a volume change rate involving no phase change of trimethylene carbonate.

Results of Comparative Examples 2 to 6 are presented in Table 5. In results of polymerization of the monofunctional TMC, the volume change rate was −0.97%, exhibiting slight shrinkage (FIG. 2). In addition, as an amount of TMC is increased, the glass transition temperature is decreased, which is disadvantageous in terms of heat resistance.

TABLE 5

|  | Comparative Example 2 | Comparative Example 3 | Comparative Example 4 | Comparative Example 5 | Comparative Example 6 |
|---|---|---|---|---|---|
| YL-980 | 2 | 2 | 2 | 2 | 2 |
| OXT-211 (POX) | 10 | 9.64 | 9.17 | 8.81 | 7.62 |
| CEL2000 | 1 | 0.96 | 0.91 | 0.87 | 0.74 |
| TMC | – | 0.40 | 0.92 | 1.32 | 2.64 |
| PI2074 | 0.2 | 0.2 | 0.2 | 0.2 | 0.2 |
| Volume change rate (%) | −5.45 | −5.36 | −5.02 | −4.90 | −4.56 |
| Tg (° C.) | 38.8 | 35.4 | 30.9 | 30> | 30> |

The unit of the numerals of the materials in Table 5 is "parts by mass".

Volume Change Rates and Tgs of Comparative Examples 7 to 10

Figure 3:
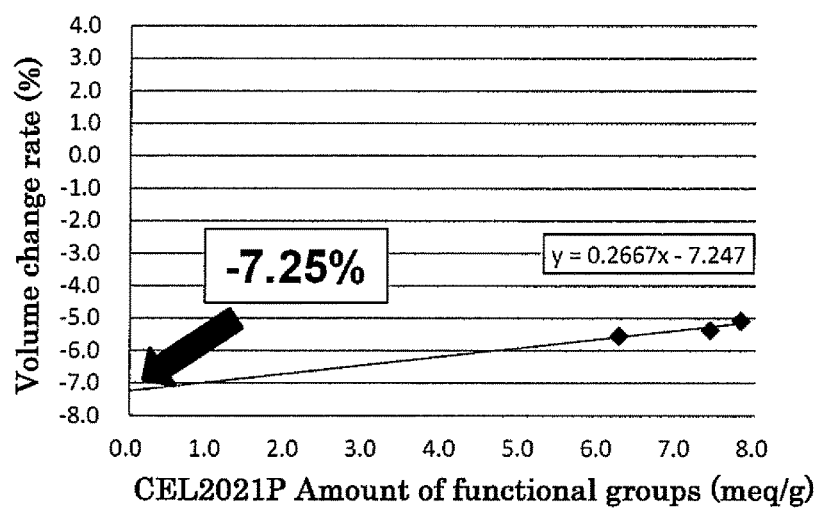
FIG. 3 is a graph for calculating a volume change rate involving no phase change of a Bis-A type epoxy resin.
Figure 4:
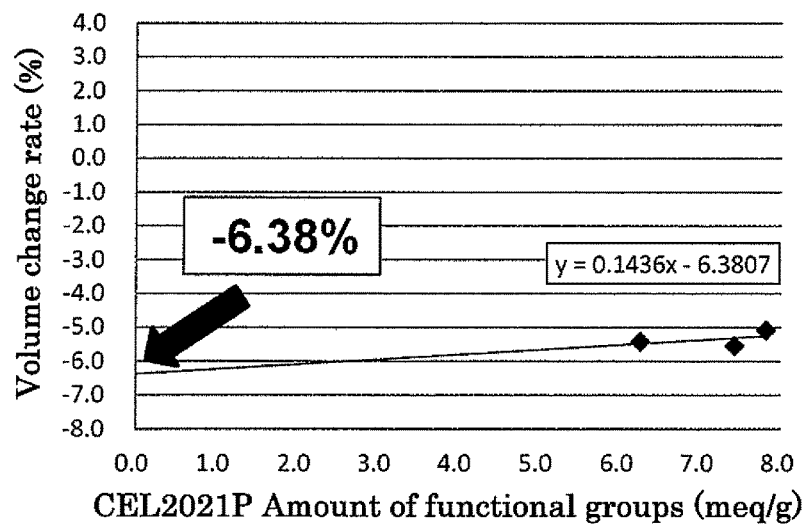
FIG. 4 is a graph for calculating a volume change rate involving no phase change of a bifunctional epoxy including a bisphenyl fluorene.

Results of Comparative Examples 7 to 10 are presented in Table 6. When 5 parts by mass of YL-980, which is a typical Bis-A type epoxy resin, was added, the volume change rate was −5.37%. When 5 parts by mass of the bifunctional epoxy including the bisphenyl fluorene was added, the volume change rate was −5.55%. When 10 parts by mass of YL-980 was added, the volume change rate was −5.56%. When 5 parts by mass of the bifunctional epoxy including the bisphenyl fluorene was added, the volume change rate was −5.43%. Therefore, the YL-980 and the bifunctional epoxy including the bisphenyl fluorene exhibit high shrinkage through curing (FIGS. 3 and 4).

When the volume change rate relative to 100% of each compound was calculated in the same manner as in Example 2, the volume change rate of YL-980 was −7.25% and the volume change rate of the bifunctional epoxy including the bisphenyl fluorene was −6.38%, exhibiting cure shrinkage.

The glass transition temperatures of Comparative Examples 7 to 10 are 194° C., 192° C., 188° C., and 184° C., respectively, exhibiting high heat resistance.

TABLE 6

|  | Comparative Example 7 | Comparative Example 8 | Comparative Example 9 | Comparative Example 10 |
|---|---|---|---|---|
| CEL2021P | 95 | 90 | 95 | 90 |
| YL-980 | 5 | 10 | — | — |
| OGSOL EG-200 | — | — | 5 | 10 |
| PI2074 | 2 | 2 | 2 | 2 |
| Volume change rate (%) | −5.37 | −5.56 | −5.55 | −5.43 |
| Tg (° C.) | 194 | 192 | 188 | 184 |

The unit of the numerals of the materials in Table 6 is "parts by mass".

INDUSTRIAL APPLICABILITY

The fluorene derivative of the present invention achieves both heat resistance and low cure shrinkage and can be suitably used as an adhesive material for connecting electronic components.

This application claims priority to Japanese application No. 2017-013539, filed on Jan. 27, 2017 and incorporated herein by reference.

What is claimed is:

1. A fluorene derivative represented by General Formula (1) below:

$$X^1-Y-X^2 \qquad \text{General Formula (1)}$$

where in the General Formula (1), $X^1$ represents a cyclic carbonate group including a carbonate bond [—O—C(=O)—O—], $X^2$ represents a cyclic carbonate group including a carbonate bond [—O—C(=O)—O—], and Y represents a bivalent group represented by General Formula (Y1) below:

General Formula (Y1)

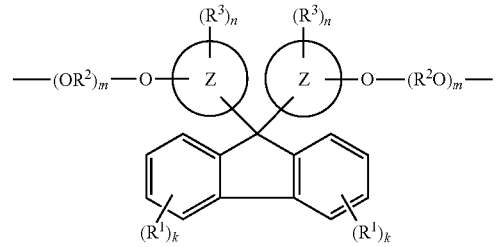

where in the General Formula (Y1), ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an arallcyloxy group, an alkylthio group, a cycloalkylthio group, an arylthio group, an aralkylthio group, an acyl group, an alkoxycarbonyl group, a hydroxy group, a halogen atom, a nitro group, a cyano group, or a dialkyamino group, k each independently represents an integer of 0 to 4, m each independently represents an integer of 0 or 1 or more, and n each independently represents an integer of 0 or 1 or more.

2. The fluorene derivative according to claim 1, wherein the group represented by the $X^1$ is a group represented by General Formula (X1) below and the group represented by the $X^2$ is a group represented by General Formula (X2) below:

General Formula (X1)

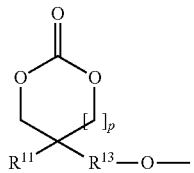

General Formula (X2)

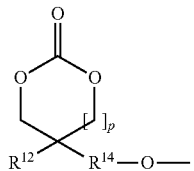

where in the General Formula (X1), $R^{11}$ represents an alkyl group, $R^{13}$ represents an alkylene group, and p represents 0 or 1; and in the General Formula (X2), $R^{12}$ represents an alkyl group, $R^{14}$ represents an alkylene group, and p represents an integer of 0 or 1.

3. The fluorene derivative according to claim 1, wherein the fluorene derivative is represented by General Formula (Z31) below:

General Formula (Z31)

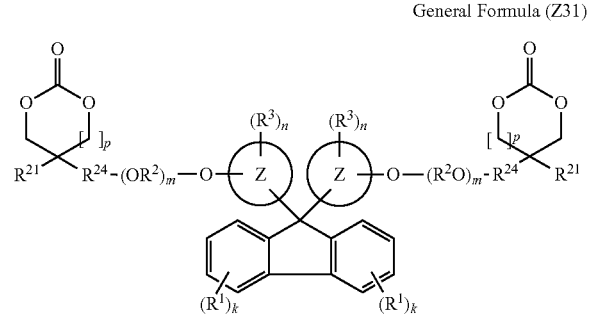

where in the General Formula (Z31), $R^{21}$ each represents an alkyl group, $R^{24}$ each represents an alkylene group, ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a dialkylamino group, k each independently represents an integer of 0 to 4, m each independently represents an integer of 0 or 1 or more, n each independently represents an integer of 0 or 1 or more, and p each represents an integer of 0 or 1.

4. The fluorene derivative according to claim 1, wherein the fluorene derivative is represented by General Formula (Z32) below:

General Formula (Z32)

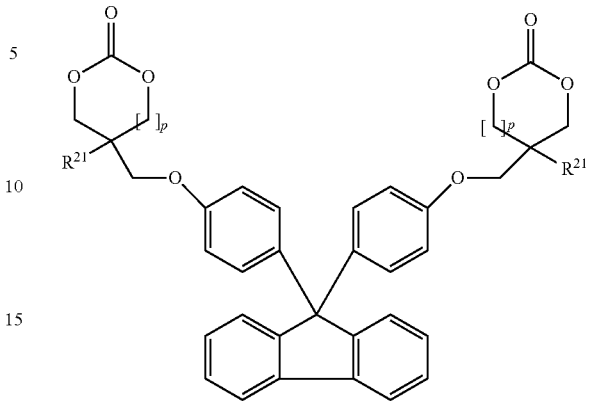

where in the General Formula (Z32), $R^{21}$ each represents an alkyl group, and p each represents an integer of 0 or 1.

5. A resin composition comprising
the fluorene derivative according to claim 1.

6. The resin composition according to claim 5, further comprising
an epoxy compound.

7. The resin composition according to claim 6, wherein a mass ratio between the fluorene derivative and the epoxy compound (the fluorene derivative:the epoxy compound) is 0.1:99.9 to 15:85.

8. The resin composition according to claim 6, wherein the mass ratio between the fluorene derivative and the epoxy compound (the fluorene derivative:the epoxy compound) is 1:99 to 5:95.

9. The resin composition according to claim 5, wherein a volume change rate before and after curing is 5.00% or less.

10. An article comprising
a cured product of the resin composition according to claim 5.

11. A method for producing a fluorene derivative, the method comprising:
reacting a compound represented by General Formula (X3) below with a compound represented by General Formula (Y21) below to obtain a fluorene derivative represented by General Formula (Z11) below;
converting the fluorene derivative represented by General Formula (Z11) into a fluorene derivative represented by General Formula (Z21) below; and
converting the fluorene derivative represented by General Formula (Z21) into a fluorene derivative represented by General Formula (Z31) below to obtain the fluorene derivative represented by General Formula (Z31), General Formula (X3)

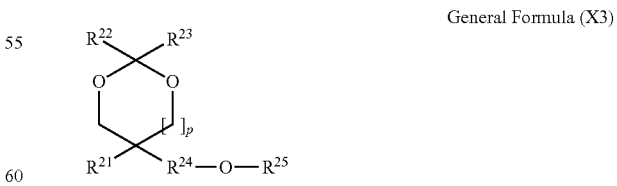

where in the General Formula (X3), $R^{21}$ each represents an alkyl group, $R^{22}$ each represents an alkyl group, $R^{23}$ each represents an alkyl group, $R^{24}$ each represents an alkylene group, $R^{25}$ represents a para-toluenesulfonyl group or an alkylsulfonyl group, and p each represents an integer of 0 or 1, General Formula (Y21)

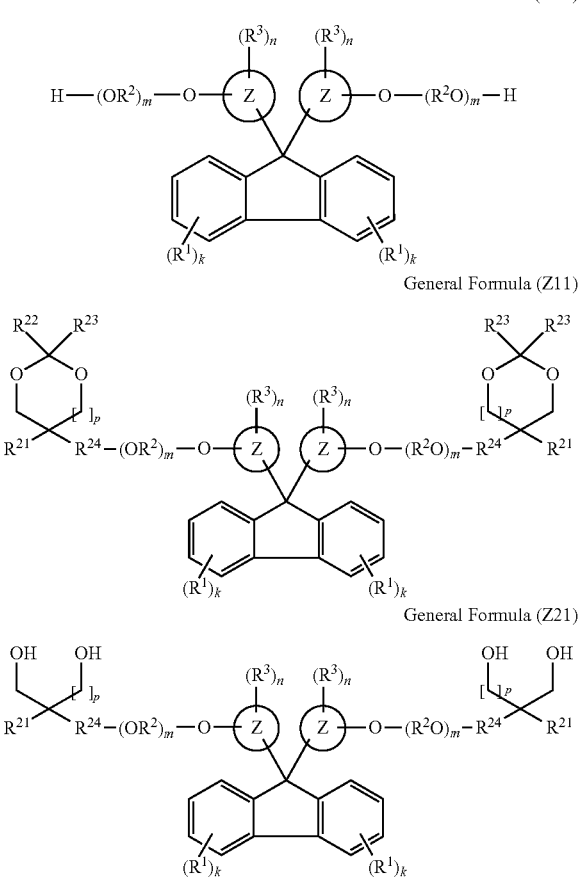

General Formula (Z31)

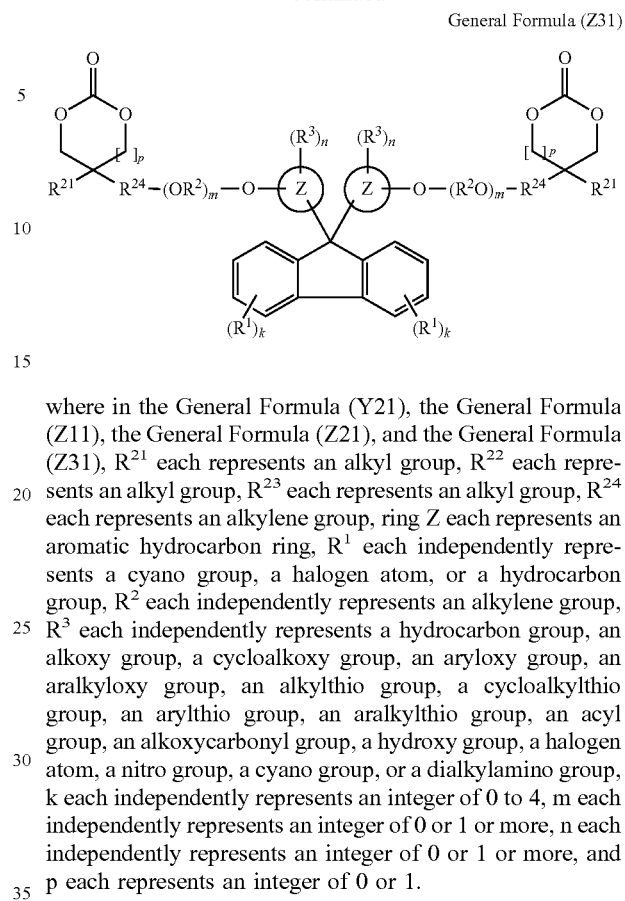

where in the General Formula (Y21), the General Formula (Z11), the General Formula (Z21), and the General Formula (Z31), $R^{21}$ each represents an alkyl group, $R^{22}$ each represents an alkyl group, $R^{23}$ each represents an alkyl group, $R^{24}$ each represents an alkylene group, ring Z each represents an aromatic hydrocarbon ring, $R^1$ each independently represents a cyano group, a halogen atom, or a hydrocarbon group, $R^2$ each independently represents an alkylene group, $R^3$ each independently represents a hydrocarbon group, an alkoxy group, a cycloalkoxy group, an aryloxy group, an aralkyloxy group, an alkylthio group, a cycloalkylthio group, an arylthio group, an aralkylthio group, an acyl group, an alkoxycarbonyl group, a hydroxy group, a halogen atom, a nitro group, a cyano group, or a dialkylamino group, k each independently represents an integer of 0 to 4, m each independently represents an integer of 0 or 1 or more, n each independently represents an integer of 0 or 1 or more, and p each represents an integer of 0 or 1.

* * * * *